(12) United States Patent
Sinkler et al.

(10) Patent No.: US 7,972,989 B2
(45) Date of Patent: Jul. 5, 2011

(54) ENHANCEMENT OF MOLECULAR SIEVE PERFORMANCE

(75) Inventors: Wharton Sinkler, Des Plaines, IL (US); Robert W. Broach, Des Plaines, IL (US); Natasha Erdman, Somerville, MA (US); Thomas M. Reynolds, Chickasaw, AL (US); John Q. Chen, Des Plaines, IL (US); Stephen T. Wilson, Des Plaines, IL (US); Paul T. Barger, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/431,297

(22) Filed: Apr. 28, 2009

(65) Prior Publication Data

US 2009/0209406 A1    Aug. 20, 2009

Related U.S. Application Data

(62) Division of application No. 11/171,801, filed on Jun. 30, 2005, now Pat. No. 7,547,812.

(51) Int. Cl.
  *B01J 27/182* (2006.01)
  *C01B 33/26* (2006.01)
(52) U.S. Cl. ........ 502/214; 423/700; 423/701; 423/702; 423/703; 423/704; 423/705; 423/706; 423/709
(58) Field of Classification Search .................. 502/214; 423/700, 701, 702, 703, 704, 705, 706, 709
See application file for complete search history.

(56) References Cited

U.S. PATENT DOCUMENTS

| | | | |
|---|---|---|---|
| 4,440,871 | A | 4/1984 | Lok et al. |
| 4,499,327 | A | 2/1985 | Kaiser |
| 5,126,308 | A | 6/1992 | Barger et al. |
| 5,248,647 | A | 9/1993 | Barger |
| 5,888,921 | A | 3/1999 | Tsang et al. |
| 5,912,393 | A | 6/1999 | Barger et al. |
| 6,620,983 | B1 | 9/2003 | Cao et al. |
| 6,793,901 | B2 | 9/2004 | Cao et al. |
| 6,953,767 | B2 | 10/2005 | Janssen et al. |
| 7,241,716 | B2 | 7/2007 | Janssen et al. |
| 7,518,026 | B2 | 4/2009 | Mertens et al. |
| 7,547,812 | B2 | 6/2009 | Sinkler et al. |
| 2002/0165090 | A1 | 11/2002 | Janssen et al. |
| 2003/0231999 | A1 | 12/2003 | Cao et al. |
| 2005/0101478 | A1 | 5/2005 | Janssen et al. |
| 2006/0074266 | A1 | 4/2006 | Mertens et al. |
| 2009/0209411 | A1 | 8/2009 | Sinkler et al. |
| 2009/0209798 | A1 | 8/2009 | Sinkler et al. |

FOREIGN PATENT DOCUMENTS

| | | |
|---|---|---|
| EP | 0324082 A1 | 7/1989 |
| EP | 1214974 A1 | 6/2002 |
| WO | WO 02/076612 A1 | 10/2002 |

*Primary Examiner* — Elizabeth D Wood
(74) *Attorney, Agent, or Firm* — Mark Goldberg

(57) ABSTRACT

A catalyst for converting methanol to light olefins and the process for making and using the catalyst are disclosed and claimed. SAPO-34 is a specific catalyst that benefits from its preparation in accordance with this invention. A seed material is used in making the catalyst that has a higher content of the EL metal than is found in the principal part of the catalyst. The molecular sieve has predominantly a roughly rectangular parallelepiped morphology crystal structure with a lower fault density and a better selectivity for light olefins.

7 Claims, No Drawings

ENHANCEMENT OF MOLECULAR SIEVE PERFORMANCE

CROSS-REFERENCE TO RELATED APPLICATION

This application is a Division of application Ser. No. 11/171,801 filed Jun. 30, 2005, now U.S. Pat. No. 7,547,812, the contents of which are hereby incorporated by reference in its entirety.

FIELD OF THE INVENTION

This invention relates to a process for producing an enhanced catalyst, the catalyst and the use of this catalyst for converting oxygenates to light olefins. More particularly, the process of this invention is highly efficient in converting methanol to light olefins due to the use of catalysts having a favorable catalyst.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstocks. It has been known for some time that oxygenates, especially alcohols, e.g. methanol, are convertible into light olefin(s). The preferred methanol conversion process is generally referred to as methanol-to-olefin(s) (MTO) process, where methanol is converted to ethylene and propylene in the presence of a molecular sieve.

The limited supply and increasing cost of crude oil has prompted the search for alternative processes for producing hydrocarbon products. An important type of alternate feed for the production of light olefins are oxygenates, such as alcohols, particularly methanol and ethanol, ethers such as dimethyl ether, methyl ethyl ether, and diethyl ether, dimethyl carbonate, and methyl formate. These oxygenates may be produced by fermentation, or from synthesis gas derived from natural gas, petroleum liquids, carbonaceous materials, including coal, recycled plastics, municipal wastes, or other organic materials. One process that is particularly useful in producing olefins is the conversion of methanol to hydrocarbons and especially to light olefins. The commercial interest in the MTO process is based on the fact that methanol can be obtained from readily available raw materials such as coal or natural gas which are treated to produce synthesis gas which is in turn processed to produce methanol.

Oxygenates are converted to an olefin product through a catalytic process. The conversion of a feed containing oxygenates is usually conducted in the presence of a molecular sieve catalyst. Although ZSM-type molecular sieves and other molecular sieves may be used for the production of olefins from oxygenates, silicoaluminophosphate (SAPO) molecular sieves have been found to be of particular value in this catalytic process.

Silicoaluminophosphate molecular sieves are manufactured from sources of silicon, such as a silica sol, aluminum, such as hydrated aluminum oxide and phosphorus, such as orthophosphoric acid. In addition, an organic template such as tetraethylammonium hydroxide, isopropylamine or di-n-propylamine is used. SAPO-34 belongs to the family of molecular sieves having the structure type of the zeolitic mineral chabazite (CHA). The CHA framework type has a double six-ring structure in an ABC stacking arrangement when viewed perpendicular to the rhombohedral 3-fold axis.

The preparation and characterization of SAPO-34 has been reported in several patents including U.S. Pat. Nos. 4,440,871 and 5,248,647, both of which are herein fully incorporated by reference.

One of the most important embodiments of the MTO conversion process is directed to the production of light olefins, i.e., olefins containing from 2 to 4 carbon atoms, inclusive. Accordingly, it is important to utilize a catalyst which maximizes the production of these products, results in a high degree of conversion of the starting methanol, and does not deactivate rapidly under the process conditions imposed. In the conversion of methanol to olefins, SAPO-34 exhibits relatively high product selectivity to ethylene and propylene, and low product selectivity to paraffin and olefin with four or more carbons ($C_4+$ olefin).

The effect of the particle size of the molecular sieve on activity has also been documented in U.S. Pat. No. 5,126,308. In the '308 patent, it is disclosed that molecular sieves in which 50% of the molecular sieve particles have a particle size less than 1.0 µm and no more than 10% of the particles have a particle size greater than 2.0 µm have increased activity and/or durability. The '308 patent also discloses that restricting the silicon content to about 0.005 to about 0.05 mole fraction also improves catalytic performance.

One desirable group of silicoaluminophosphate molecular sieves is those that have low silicon content. Silicoaluminophosphates of the CHA framework type with low silicon content are particularly desirable for use in the MTO process. Low silicon content has the effect of reducing propane formation and decreasing catalyst deactivation. However, it has proven difficult to make pure phase CHA silicoaluminophosphate molecular sieves with low silica to alumina ratio.

In the art, various attempts have been made to improve the synthesis of $AlPO_4$ or SAPO molecular sieves. One approach has been the addition of a source of fluoride ions to the synthesis mixture. However, this approach has the disadvantage that many of the fluorides cause cost, safety or environmental concerns due to their toxicity, corrosiveness and volatility. It would be highly desirable to have a process that avoids their use. U.S. Pat. No. 6,620,983 B1 describes the use of other fluorine containing compounds. These compounds have two or more fluorine substituents, as the source of fluoride ion, in the synthesis of aluminophosphates or silicoaluminophosphates. Although the molecular sieves produced are described as having the desired chabazite crystal structure, they produce a lower than desired yield of light olefins when used in a methanol to olefins process. Therefore, these other fluorine containing compounds are not the solution sought. It would also be desirable to have a more effective catalyst in conversion of oxygenates to olefins.

It is therefore desirable to find new processes, which are specific for the synthesis of molecular sieves having the CHA framework type. A particular need is to find methods of preparing low silica SAPO molecular sieves, which do not require the use of hydrogen fluoride or other fluorides.

SUMMARY OF THE INVENTION

The present invention provides a method for the synthesis of metalloaluminophosphate molecular sieves that overcomes many of the problems inherent in the prior art methods of synthesis.

More specifically, the method for preparing metalloaluminophosphate molecular sieves comprises first providing a seed containing from about 5 to 20 wt-% metal oxide on a dry oxide basis and then forming a reaction mixture comprising said seeds, a source of aluminum, a source of phosphorus, at least one organic template, and, a source of metal, and then inducing crystallization of metalloaluminophosphate molecular sieve from the reaction mixture. The source of metal provides a lower concentration of metal oxide to the reaction mixture than is present in the seed. From 1-5 wt % metal oxide is present in these reaction mixtures. In a preferred embodiment of the invention, the metal is silicon and the metal oxide is SiO₂.

This invention also comprises using these silicoaluminophosphate molecular sieves as catalysts that contain binders for converting methanol to light olefins.

The invention further comprises a novel crystalline silicoaluminophosphate molecular sieve in which a first portion of the molecular sieve comprises a higher concentration of silica than does a larger second portion of the molecular sieve. In one embodiment of the invention, the first portion of the molecular sieve comprises about 5-20 wt-% silica and the larger second portion comprising the remainder of the molecular sieve comprises about 1-5 wt % silica. In the present invention, the preferred molecular sieves have a CHA framework type, AEI framework type, an intergrowth of CHA and AEI framework types or a mixture of at least two of said framework types.

DETAILED DESCRIPTION OF THE INVENTION

The process of the instant invention concerns the preparation of and the use of silicoaluminophosphate molecular sieves which is a type of ELAPO molecular sieve. Other types of aluminophosphates may be prepared as well. ELAPOs are molecular sieves which have a three-dimensional microporous framework structure of $AlO_4$, $PO_4$ and $ELO_4$ tetrahedral units. Generally the ELAPOs have the empirical formula:

$(EL_xAl_yP_z)O_2$ where EL is a metal selected from the group consisting of silicon, magnesium, zinc, iron, cobalt, nickel, manganese, chromium and mixtures thereof, "x" is the mole fraction of EL and has a value of at least 0.005, "y" is the mole fraction of Al and has a value of at least 0.01, "z" is the mole fraction of P and has a value of at least 0.01 and x+y+z=1. When EL is a mixture of metals, "x" represents the total amount of the metal mixture present. Preferred metals (EL) are silicon, magnesium and cobalt with silicon being especially preferred. The molecular sieves of the present invention are made with a seed material of higher metal content than is present in the final molecular sieve product. The seed material comprises from 5 to 20 wt % metal and preferably 8 to 15 wt % metal and most preferably 10 to 15 wt % metal. A lower level of metal content is found in the other ingredients that are used to prepare the molecular sieve product. These other ingredients comprise from 1 to 5 wt % metal and preferably 2 to 4 wt % metal.

The preparation of various ELAPOs are well known in the art. Generally, ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, sources of silicon include fumed, colloidal, precipitated or alkoxide forms of silica. Reactive sources of aluminum and phosphorus are pseudo-boehmite alumina and phosphoric acid. Templating agents that are used include amines and quaternary ammonium compounds. A frequently used templating agent is tetraethylammonium hydroxide (TEAOH).

When the molecular sieves are calcined, the resulting AlPO's or SAPO's have an x-ray diffraction (XRD) pattern typical of the CHA framework type and are of high purity in terms of their framework type. Seed crystals having higher silicon concentration than the desired molecular sieve are used to produce the CHA framework type crystals. Without the use of the seed crystals of higher silicon concentration than the remainder of the reaction mixture, the intergrowth content is higher.

The reaction mixture, consisting of a source of aluminum, a source of phosphorous, one or more templating agents, seed crystals, and, one or more metal containing compounds is placed in a sealed pressure vessel, optionally lined with an inert plastic material such as polytetrafluoroethylene and heated preferably under autogenous pressure at a temperature between about 50° and 250° C. and preferably between about 100° and 200° C. for a time sufficient to produce crystals. Typically, the time varies from about 1 to about 120 hours and preferably from about 24 to about 48 hours. The desired product is recovered by any convenient separation method such as centrifugation, filtration or decanting.

The molecular sieves of the present invention may be combined with one or more formulating agents, to form a molecular sieve catalyst composition or a formulated molecular sieve catalyst composition. The formulating agents may be one or more materials selected from the group consisting of binding agents, matrix or filler materials catalytically active materials and mixtures thereof. This formulated molecular sieve catalyst composition is formed into useful shape and sized particles by well-known techniques such as spray drying, pelletizing, or extrusion. Matrix materials are typically effective in reducing overall catalyst cost, in acting as thermal sinks that assist in shielding heat from the catalyst composition, for example, during regeneration, densifying the catalyst composition, increasing catalyst strength such as crush strength and attrition resistance, and in controlling the rate of conversion in a particular process.

Upon combining the molecular sieve and the matrix material, optionally with a binder, in a liquid to form a slurry, mixing, preferably rigorous mixing, is needed to produce a substantially homogeneous mixture containing the molecular sieve. Examples of suitable liquids include water, alcohol, ketones, aldehydes, esters and combinations thereof. The most preferred liquid is water. The slurry may be colloid-milled for a period of time sufficient to produce the desired slurry texture, sub-particle size, and/or sub-particle size distribution.

The molecular sieve and matrix material, and the optional binder, may be in the same or different liquids, and may be combined in any order, either together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of smaller particles that is then fed to a forming unit to produce the molecular sieve catalyst composition. A spray dryer is often used as the forming unit. Typically, the forming unit is maintained at a temperature sufficient to remove most of the liquid from the slurry, and from the resulting molecular sieve catalyst composition. The resulting catalyst composition when formed in this way takes the form of microspheres.

Generally, the particle size of the powder is controlled to some extent by the solids content of the slurry. However, the particle size of the catalyst composition and its spherical characteristics are also controllable by varying the slurry feed properties and conditions of atomization. Also, although spray dryers produce a broad distribution of particle sizes, classifiers are normally used to separate the fines which can then be milled to a fine powder and recycled to the spray dryer feed mixture.

After the molecular sieve catalyst composition is formed in a substantially dry or dried state, a heat treatment such as calcination, at an elevated temperature is usually performed to further harden and/or activate the formed catalyst composition. A conventional calcination environment is air that typically includes a small amount of water vapor. Typical calcination temperatures are in the range from about 400° to about 1000° C., preferably from about 500° to about 800° C., and most preferably from about 550° to about 700° C. The calcination environment is a gas such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the desired degree of hardening of the molecular sieve catalyst composition and the temperature.

In one embodiment, the molecular sieve catalyst composition is heated in nitrogen at a temperature of from about 600° to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

In addition to the molecular sieve of the present invention, the catalyst compositions of the present invention may comprise one or several other catalytically active materials.

The molecular sieve catalysts and compositions of the present invention are useful in a variety of processes including: cracking, hydrocracking, isomerization, polymerization, reforming, hydrogenation, dehydrogenation, dewaxing, hydrodewaxing, absorption, alkylation, transalkylation, dealkylation, hydrodecyclization, disproportionation, oligomerization, dehydrocyclization and combinations thereof.

The catalyst prepared in accordance with the present invention is particularly useful in a process directed to the conversion of a feedstock comprising one or more oxygenates to one or more olefin(s). Preferably, the oxygenate in the feedstock comprises one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, preferably comprising one or more oxygenates, is converted in the presence of a molecular sieve catalyst composition into one or more olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The process of converting methanol to olefins is generally referred to as "MTO". In an MTO process, an oxygenated feedstock, containing methanol as a primary component of the feedstock, is converted in the presence of a molecular sieve catalyst composition into one or more olefin(s), predominantly, ethylene and/or propylene, often referred to as light olefin(s). The amount of light olefin(s) produced based on the total weight of hydrocarbon produced is at least 50 wt-%, preferably greater than 60 wt-%, more preferably greater than 70 wt-%. Higher yields may be obtained through improvements in the operation of the process as known in the art.

The feedstock may contain at least one or more diluents, typically used to reduce the concentration of the feedstock that is reactive toward the molecular sieve catalyst composition. Examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The preferred diluents are water and nitrogen, with water being particularly preferred. Water, can be used either in a liquid or a vapor form, or a combination thereof. The diluent is either added directly to a feedstock entering into a reactor or added directly into a reactor, or added with a molecular sieve catalyst composition. The amount of diluent in the feedstock is generally in the range of from about 5 to about 50 mol-% based on the total number of moles of the feedstock and diluent, and preferably from about 5 to about 25 mol-%.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like.

In the preferred embodiment, a fluidized bed process or high velocity fluidized bed process includes a reactor system, a regeneration system and a product recovery system.

The fluidized bed reactor system has a first reaction zone within one or more riser reactor(s) and a second reaction zone within at least one disengaging vessel, preferably comprising one or more cyclones. The riser reactor(s) and disengaging vessel are contained within a single reactor vessel. Fresh feedstock is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

If regeneration is required, the silicoaluminophosphate molecular sieve catalyst can be continuously introduced as a moving bed to a regeneration zone where it can be regenerated, such as, for example, by removing carbonaceous materials by oxidation in an oxygen-containing atmosphere. In the preferred practice of the invention, the catalyst will be subject to a regeneration step by burning off carbonaceous deposits accumulated during reactions.

In converting methanol to olefins using the catalyst compositions of the invention, the process is preferably carried out in the vapor phase such that the feedstock is contacted in a vapor phase in a reaction zone with a silicoaluminophosphate molecular sieve at effective process conditions such as to produce light olefins, i.e., an effective temperature, pressure, WHSV (weight hourly space velocity) and, optionally, an effective amount of diluent, correlated to produce light olefins. Alternatively, the process may be carried out in a liquid phase. When the process is carried out in the liquid phase, the process necessarily involves the separation of products formed in a liquid reaction media and can result in different conversions and selectivities of feedstock to product with respect to the relative ratios of the light olefin products as compared to that formed by the vapor phase process.

The temperatures which may be employed in the process may vary over a wide range depending, at least in part, on the selected silicoaluminophosphate catalyst. In general, the process can be conducted at an effective temperature between about 200° and about 700° C., preferably between about 250° and about 600° C., and most preferably between about 300° and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° and about 700° C.

The process is effectively carried out over a wide range of pressures including autogenous pressures. At pressures between about 0.001 atmospheres and about 1000 atmospheres, light olefin products will not necessarily form at all pressures. The preferred pressure is between about 0.01 atmospheres and about 100 atmospheres. The pressures referred to herein for the process are exclusive of the inert diluent, if any is present, and refer to the partial pressure of the feedstock as it relates to methanol. Pressures outside the stated range are not excluded from the scope of this invention, although such do not fall within certain desirable embodiments of the invention. At the lower and upper end of the pressure range, light olefin products can be formed but the process will not be optimum.

The process is run for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the silicoaluminophosphate molecular sieve selected, the weight hourly space velocity (WHSV), the phase (liquid or vapor) selected and, perhaps, selected reactor design characteristics.

The process is effectively carried out over a wide range of WHSV for the feedstock and is generally between about 0.01 and about 100 $hr^{-1}$ and preferably between about 0.1 and about 40 $hr^{-1}$. Values above 100 $hr^{-1}$ may be employed and are intended to be covered by the instant process, although such are not preferred.

The instant process is most preferably carried out under process conditions comprising a temperature between about 300° and about 500° C., a pressure between about 0.1 atmosphere (one atmosphere equals 14.7 psia) and about 100 atmospheres, utilizing a WHSV expressed in $hr^{-1}$ for each component of the feedstock having a value between about 0.1 and about 40. The temperature, pressure, and WHSV are each selected such that the effective process conditions, i.e., the effective temperature, pressure, and WHSV are employed in conjunction, i.e., correlated, with the selected silicoaluminophosphate molecular sieve and selected feedstock such that light olefin products are produced.

The amount of fresh feedstock fed separately or jointly with a vapor feedstock, to the reactor system is in the range of from 0.1 to about 85 wt-%, preferably from about 1 to about 75 wt-%, more preferably from about 5 to about 65 wt-% based on the total weight of the feedstock including any diluent contained therein. The liquid and vapor feedstocks are preferably the same composition, or contain varying proportions of the same or different feedstock with the same or different diluent.

Molecular sieves of this invention have a roughly rectangular parallelepiped crystal morphology or intergrowth of roughly rectangular parallelepiped crystal morphologies or a mixture thereof. This includes crystals which are cubic in which all the dimensions are the same, but also those in which the aspect ratio is less than or equal to 5 and preferably less than or equal to two. It is also necessary that the average smallest crystal dimension be at least 50 nanometers and preferably at least 100 nanometers.

As is explained in the examples, the morphology of the crystals and the average smallest crystal dimension is determined by examining the ELAPO molecular sieve using scanning electron microscopy (SEM) and measuring the crystals in order to obtain an average value for the smallest dimension.

Without wishing to be bound by any one particular theory, it appears that a minimum thickness is required so that the diffusion path for desorption of ethylene and propylene is sufficiently long to allow differentiation of the two molecules. The ELAPOs and more particularly, the silicoaluminophosphates which are synthesized using the process described above will usually contain some of the organic templating agent in its pores. In order for the ELAPOs to be active catalysts, the templating agent in the pores must be removed by heating the ELAPO powder in an oxygen containing atmosphere at a temperature of about 200° to about 700° C. until the template is removed, usually a few hours.

A preferred embodiment of the invention is one in which the metal (EL) content varies from about 0.005 to about 0.05 mole fraction. An especially preferred embodiment is one in which EL is silicon (usually referred to as SAPO). The SAPOs which can be used in the instant invention are any of those described in U.S. Pat. No. 4,440,871. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 angstroms. SAPO-34 is a silica-aluminophosphate material with the chabazite (CHA) framework structure. The structure is rhombohedral and can be described as a stacking of sheets along <100> directions in the crystal structure. The sheets contain slanted double six rings. In successive sheets all double six rings are slanted in the same direction giving an AAAA stacking sequence along the rhombohedral <100> directions. If the direction of slant is reversed every second plane, creating an ABABAB stacking sequence, the ALPO-18 structure (AEI) results. Both of these structure types consist of the same sheet structure, stacked with a different sequence, either AAAA (CHA) or ABAB (AEI). This similarity is the basis for faulting representing a mixture of stacking sequences intermediate between these end members. Many SAPO-34 materials show at least some degree of faulting, as evidenced by broadening of x-ray diffraction peaks and streaking of reflections in electron diffraction patterns.

By varying the composition, specifically Si/(Al+P), over broad ranges, the degree of faulting can be influenced and there is a trend such that high Si/(Al+P) materials show less faulting, all other factors of synthesis being equal. This is found for a variety of formulations. However, the degree of faulting is quite sensitive to a number of factors and exceptions to the trend can be expected for different syntheses in a narrow range of Si/(Al+P) ratio.

Varying compositions can also influence particle morphology. In general for SAPO-34 preparations at greater than 5 wt-% $SiO_2$ in the final product, the morphology is roughly described as cube-like, whereas most but not all materials produced in the range below about 4 wt-% $SiO_2$ in the final product tend to have a plate-like morphology. In fact, morphology and degree of faulting were found to be correlated. The faults break the rhombohedral symmetry by distinguishing one of the otherwise equivalent <100> planes; crystals grow more rapidly in the unfaulted directions and a plate-like morphology tends to result.

It has been found that the selectivity of the reaction to $C_2$ and $C_3$ olefins in the MTO reaction process is negatively impacted by large fault densities (as determined by x-ray diffraction of calcined SAPO-34 compounds).

It has further been found that a more three-dimensional morphology, being either cube-like or consisting of intersecting plates (with faults along distinct <100> planes) is beneficial to selectivity in the MTO reaction.

These factors indicate that a high ratio of Si/(Al+P) would be desirable in SAPO-34 for use in the MTO process. Unfortunately, it has been found that increasing the silica level raises the acidity of the catalyst which may accelerate catalyst sensitivity to deactivation by coking.

A method of producing SAPO-34 catalyst having the desired morphology has now been discovered. This method measurably decreases the AEI fault density without increasing the overall silicon level. It also increases the degree of desirable roughly rectangular parallelepiped crystal morphology growth as opposed to less desirable plate-like growth and allows the morphology of the crystals to be influenced without increasing the level of silicon in the SAPO-34 crystal.

The key to the method of preparation of the molecular sieves in the present invention is the use of seeds that have a relatively high Si/(Al+P) level. The high silicon level in the seeds results in SAPO-34 crystals that are relatively fault-free. Without wishing to be bound by a particular theory as to the mechanism involved, the use of the seeds in the synthesis of SAPO-34 results in SAPO-34 having a lower fault density than obtained without the use of the seeds. The seeds themselves are cube-like and present surfaces for nucleation of subsequent growth in all three directions, resulting in a morphology which is three-dimensional, as opposed to simple cubes. The seeds used in the present invention preferably contain from about 5 to 20 wt-% $SiO_2$, more preferably contain about 8 to 15 wt-% $SiO_2$ and most preferably contain about 10 to 15 wt-% $SiO_2$. The following table shows that when seeds containing less than 3 wt-% $SiO_2$ are used, the selectivity to production of the desired ethylene and propylene was about 81% and when the seeds having $SiO_2$ in the desired range was used, the selectivity was about 85%.

| Sample No. | $SiO_2$, wt-% volatile free | Selectivity for ethylene and propylene wt-% | Seed quantity as wt-% of dry product | Seed $SiO_2$ wt-%, volatile free |
|---|---|---|---|---|
| 1 | 3.2 | 81 | 0.4 | 2.8 |
| 2 | 3.2 | 84.9 | 4.0 | 14.7 |
| 3 | 2.7 | 84.7 | 4.0 | 12.1 |
| 4 | 3.6 | 84.3 | 4.0 | 9.0 |

An increase of yield in this amount is considered significant in improving the efficiency and profitability of an MTO plant. Sample 1 is of a prior art material made without use of the seeds having a higher level of $SiO_2$ while Samples 2-4 are samples within the scope of the present invention that were prepared in accordance with the method described in the following Example.

EXAMPLE

A quantity of catalyst prepared in accordance with the present invention was made. In a container, 345 grams of orthophosphoric acid (85%) was combined with 403 grams of water. To this mixture was added 30 grams of a silica suspension (Ludox LS, Aldrich Chemicals) and 628 grams of a 35 wt-% aqueous solution of tetraethylammonium hydroxide (TEAOH). Then 212 grams alumina in the form of pseudo-boehmite, (sold by UOP LLC as Versal 250) along with water and 18 grams of SAPO-34 seed material containing about 9 wt-% silica were added and blended in. In addition, a quantity of catalyst was made without the higher silica seeds that are used in the present invention for purposes of comparison The mixtures were then placed in a steel pressure reactor equipped with a turbine stirrer. The mixtures were stirred and heated to 100° C. over a 6-hour period, then held at 100° C. for 9 hours, heated to 175° C. over a period of 5 hours and then held at 175° C. for 48 hours. Finally, the reaction mixture was cooled to ambient room temperature over a period of 8 hours. The solid product was recovered by centrifugation over a 20-minute period, and washed with water. A series of three additional reslurry, centrifugation, decant steps followed and then the product was dried overnight at 95° C. Several characterization methods were used to examine properties of the product including the fault density (X-ray diffraction), morphology (transmission electron microscopy and scanning electron microscopy) and chemical analysis (transmission electron microscopy).

Samples 2 and 3 showed X-ray diffraction patterns with relatively well-formed and sharp peaks indicative of crystallites with the CHA structure type and only small amounts of AEI faulting. Sample 1, exhibited broadening of some peaks and the appearance of new peaks in the diffraction pattern, indicating the presence of significant amounts of AEI faulting. Further analysis of the data confirmed these conclusions.

Scanning electron microscopy showed that the morphology of Samples 2 and 3 were consistent with cubes or thick, intergrown plates, while the morphology of Sample 1 was best described as thin plates. Transmission electron microscopy confirmed this comparison of the morphology of the samples.

Further analysis of the samples disclosed that there were often areas of elevated silicon content, typically in the center of particles, which are plausibly explained as particles of seed. Material at the edges of the particles tended to contain lower levels of silicon.

The invention claimed is:

1. A catalyst comprising a crystalline metallo-aluminophosphate molecular sieve wherein a first portion of said crystalline metallo-aluminophosphate molecular sieve comprises about 5 to 20 wt-% silica and wherein a second portion of said crystalline metallo-aluminophosphate molecular sieve comprises about 1 to 5 wt-% silica.

2. The catalyst of claim 1 wherein a first portion of said crystalline metallo-aluminophosphate molecular sieve comprises about 8 to 15 wt-% silica and wherein a second portion of said crystalline metallo-aluminophosphate comprises about 2 to 4 wt-% silica.

3. The catalyst of claim 1 where the crystalline metallo-aluminophosphate molecular sieve has the crystal structure of SAPO-34.

4. The catalyst of claim 1 comprising crystalline metallo-aluminophosphate molecular sieve and an inorganic oxide binder.

5. The catalyst of claim 4 where the inorganic oxide binder is selected from the group consisting of alumina, silica, aluminum phosphate, silica-alumina and mixtures thereof 6. The catalyst of claim 1 where the crystalline metallo-aluminophosphate molecular sieve is present in an amount from about 10 to about 90 wt-% of the catalyst.

7. The catalyst of claim 1 where the crystalline metallo-aluminophosphate molecular sieve exhibits a roughly rectangular parallelepiped crystal morphology or intergrowth of roughly rectangular parallelepiped crystal morphologies or a mixture thereof where the aspect ratio of the dimensions of the crystals largest to smallest dimension is less than or equal to 2.

* * * * *